United States Patent [19]

Siedel et al.

[11] Patent Number: 4,961,970

[45] Date of Patent: Oct. 9, 1990

[54] METHOD FOR DETERMINING IRON IN A BODY FLUID SAMPLE

[75] Inventors: Joachim Siedel, Bernried; Lieselotte Schellong, Tutzing; Johnny Staepels, Seefeld; Uwe Herrmann, Bernried; Michael-Harold Town, Oberhausen, all of Fed. Rep. of Germany

[73] Assignee: Boehringer Mannheim GmbH, Mannheim, Fed. Rep. of Germany

[21] Appl. No.: 238,620

[22] Filed: Aug. 30, 1988

[30] Foreign Application Priority Data

Sep. 3, 1987 [DE] Fed. Rep. of Germany ....... 3729502

[51] Int. Cl.$^5$ ............................................ G01N 33/20
[52] U.S. Cl. ......................................... 436/84; 436/74; 436/164; 436/910
[58] Field of Search ................... 436/74, 84, 164, 910

[56] References Cited

U.S. PATENT DOCUMENTS 4,407,962 10/1983 Tabacco et al. ..................... 436/84
4,579,825 4/1986 Siedel et al. ........................... 436/71

*Primary Examiner*—Robert J. Warden
*Assistant Examiner*—Lyle Alfandary-Alexander
*Attorney, Agent, or Firm*—Felfe & Lynch

[57] ABSTRACT

The present invention provides a process for the determination of iron in body fluids by liberation of the bound iron, reduction to $Fe^{2+}$, addition of a color system appropriate for the detection of iron and photometric measurement in a tenside-containing sample solution, wherein a fatty acid polyethylene glycol ester, an alkanol polyglycol ether and at least 1 mole/liter quanidine hydrochloride are added to the sample solution. The present invention also provides a reagent for the determination of iron in serum, containing a reducing agent, a color material system appropriate for the detection of iron and guanidine hydrochloride and at least one tenside, wherein it contains a fatty acid polyethylene glycol ester and a alkanol polyglycol ether.

15 Claims, 2 Drawing Sheets

METHOD FOR DETERMINING IRON IN A BODY FLUID SAMPLE

The present invention is concerned with a process for the determination of iron in body fluids by the liberation of bound iron, reduction to $Fe^{2+}$, addition of a color system appropriate for the detection of iron and photometric measurement in a tenside-containing sample solution, as well as a reagent suitable therefor.

Iron metabolism disturbances, especially iron deficiency and iron resorption disturbances, are especially widely occurring in the female population. Therefore, the detection of iron in body fluids, especially in serum, is one of the standard determinations in medical analysis. Iron is introduced with the food and is taken up via the mucous membrane of the intestines. Bound to transferrin in a trivalent state, it is then transported to the bone marrow where it is mainly incorporated into hemoglobin. If too little iron is taken in, then this results in anemic conditions.

The determination of iron in serum is one of the most frequently performed trace element analyses in clinical diagnosis, numerous processes being known for this purpose. Thus, in Clin. Chem., 26, 327-331/1980, a process is described in which the trivalent iron bound to transferrin in the form of a carbonate complex is liberated in a strongly acidic medium. It is a disadvantage of this process that the strongly acidic reagents display corrosive and corroding properties. In order to overcome this disadvantage, it is known, for example, from Clin. Chem., 23, 237-240/1977 and from Z. Klin. Chem., 3, 96-99/1965, to use protein-denaturing agents, for example concentrated guanidine hydrochloride, or anionic detergents for the liberation of the iron. However, this process is not suitable for carrying out the determination of iron in triglyceride rich sera, also known as lipemic sera, since neither guanidine hydrochloride nor the anion detergents have sufficient clarification power for these sera. Since iron only occurs in a very low concentration in serum, for measurement technical reasons the ratio of sample to reagent volume must be very high and is usually 1:5 and higher so that the turbidity in the test batch, which can sometimes be very great, prevents photometric measurement or falsifies the measurement.

In order to solve this problem, it has been suggested in U.S. Pat. No. 4,579,825 to use a mixture of non-ionic and anionic detergents for the liberation of the iron in a weakly acidic medium. However, it has been found that, in the case of the use of the detergents, clarification of lipemic sera admittedly takes place quickly and completely but for sera with a high content of immunoglobulin (gammopathic sera), turbidity formation is observed which falsifies the result of the measurement. Furthermore, determination of strongly hemolytic sera is not completely satisfactory.

Therefore, there is a need for a process and a reagent for the determination of iron in serum in which, on the one hand, harsh components do not have to be used and, on the other hand, rapid, complete and lasting clarification is achieved even in the case of strongly lipemic sera without the measurement being disturbed by hemolytic samples or sera with increased immunoglobulin content.

For reasons of being able to automate and for simplification, it is desirable to carry out this process without it being necessary to carry out a preceding deproteinisation of the sample.

Thus, according to the present invention, there is provided a process for the determination of iron in body fluids, such as serum, by liberation of the bound iron, reduction to $Fe^{2+}$, addition of a color system appropriate for the detection of iron and photometric measurement in a tenside-containing sample solution, wherein a fatty acid polyethylene glycol ester, an alkanol-polyglycol ether and at least 1 mole/liter guanidine hydrochloride are added to the sample solution.

Surprisingly, we have ascertained that an addition of the combination according to the present invention of fatty acid polyethylene glycol ester, alkanol-polyglycol ether and guanidine hydrochloride causes lasting and complete clarification of the sample, even when it is lipemic sera, without turbidities occurring again in the case of gammopathic sera and without disturbances being observed in the case of hemolytic samples.

For the determination of iron in serum, a fatty acid polyethylene glycol ester, an alkanol-polyglycol ether and at least 1 mole/liter guanidine hydrochloride are added to the sample solution. In this way, the iron is liberated from its transport protein, transferrin.

As fatty acid polyethylene glycol esters, there are preferably used esters of a polyethylene glycol with an average molecular weight in the range of from 200 to 600 (hereinafter also referred to as PEG 200 and PEG 600, respectively) in which a hydroxyl group is esterified with a linear fatty acid, whereas the other hydroxyl group is either free or esterified with a short-chained acid, for example acetic acid. As linear fatty acids, there are especially preferred the saturated fatty acids with 10 to 14 carbon atoms in the molecule. Polyethylene glycol monolaurate is especially preferred.

The fatty acid polyethylene glycol ester is preferably used in a concentration of from about 2.5 to 15%. Especially preferred is a concentration of from about 5 to about 10%, referred to the sample solution.

As second component, an alkanol polyglycol ether is used. Polyglycols, whose hydroxyl groups are etherified with linear or branched-chained alkanol, e.g. can be used. Polyglycols are preferably used which, on average, contain 3 to 6 glycol units. The alkanols preferably contain 8 to 12 carbon atoms in the chain. Polyglycol ethers of branchedchained alkanols are especially preferred, particularly an ether of a polyglycol with 4 glycol units and an isodecanol.

The alkanol polyglycol ether is preferably used in a concentration of from 0.5 to 5% and an especially preferred concentration is one of from 1 to 3%.

Furthermore, guanidine hydrochloride is added to the sample solution. The concentration of the guanidine hydrochloride should be relatively high, at least 1 mole/liter of guanidine hydrochloride having to be present in the sample solution. In the case of lower concentrations of guanidine hydrochloride, satisfactory and sufficiently rapid dissolving off of the iron from the transferrin is not achieved. Up to 6 mole/liter of guanidine hydrochloride is preferred in the process according to the present invention. A larger amount of guanidine hydrochloride does not result in any further improvement and is, therefore, not economical. The guanidine hydrochloride is preferably used in the range of from 3 to 5 mole/liter.

For carrying out the process according to the present invention, the sample solution is buffered in a weakly acidic range. Especially preferred is a process in which the sample is buffered at a range from a pH about 5 to about 6. As buffer substances, compounds can be used which have a pK value of 5 to 6. However, only compounds can be used which do not complex iron. Thus, for example, there can be used acetate, phosphate, succinate and tris buffer, acetate buffer preferably being used as buffer substance. The buffer is preferably used in a concentration of from 20 to 500 mMole/liter and is especially preferred in a concentration of from 50 to 150 mMole/liter.

For the determination of the iron, a reducing agent, for example ascorbic acid is then added to the sample solution in order to reduce the liberated iron, present in the trivalent form, into the divalent form. Furthermore, a color system appropriate for the detection of iron is added. Especially preferred are complex formers of the ferroin type which give a colored material with iron which can be photometrically evaluated. Examples of appropriate substances include bathophenanthroline and 3-(2-pyridyl)-5,6-bis(4-phenylsulfonic acid)-1,2,4-triazine-disodium salt. The colored material formation thereby takes place proportionally to the iron content of the sample and can be photometrically evaluated in known manner.

By means of the use of the combination according to the present invention, in the case of the photometric determination of the colored material, no disturbance occurs due to precipitations or turbidities.

For carrying out the process in accordance with the present invention, a reagent for the determination of iron in body fluids, especially in serum can be used which contains a reducing agent, a colored material system appropriate for the detection of iron, as well as guanidine hydrochloride and at least one tenside, wherein the tenside contains a fatty acid polyethylene glycol ester, and an alkanol polyglycol ether.

This reagent is especially suitable for the determination of iron in lipemic, hemolytic and/or immunoglobulin-rich body fluids, especially in sera.

DETAILED DESCRIPTION OF PREFERRED EMBODIMENTS

Example 1

Iron was determined in a human serum sample. For this purpose, the following reagents were used:

|  | sample reagent | blank value reagent |
| --- | --- | --- |
| guanidine hydrochloride | 4.5 mole/l. | 4.5 mole/l. |
| acetate buffer (pH 5.0) | 0.15 mole/l. | 0.15 mole/l. |
| isodecanol polyglycol ether | 2.0% (v/v) | 2.0 (v/v) |
| polyethylene glycol 400 monolaurate | 10.0% (v/v) | 10.0% (v/v) |
| ascorbic acid | 0.023 mole/l. | 0.023 mole/l. |

|  | sample reagent | blank value reagent |
| --- | --- | --- |
| Ferrozin ®* | 1.6 mMole/l. | — |

*3-(2-pyridyl)-5,6-bis(4-phenylsulfonic acid)-1,2,4-triazine-disodium salt

The iron determination was carried out in cuvettes with a layer thickness of 1 cm.

The reagents were pipetted into two cuvettes, the sample being measured in one cuvette and the sample blank value in the second cuvette.

|  | sample blank value | sample |
| --- | --- | --- |
| blank value reagent | 1.0 ml. | — |
| sample reagent | — | 1.0 ml. |
| sample | 0.2 ml. | 0.2 ml. |

In each case, the solutions were mixed in the cuvette and incubated for 10 minutes at 25° C. Within the course of a further 30 minutes, there was measured, at a wavelength of 562 nm or of Hg 578 nm, the extinction of the sample blank value against a mixture of 1 ml. of blank value reagent and 0.2 ml. distilled water ($E_{PL}$), as well as the sample against a mixture of 1 ml of sample reagent and 0.2 ml distilled water ($E_P$) The value for the extinction difference is then given as:

$$E = E_P - E_{PL}$$

Figure 1:
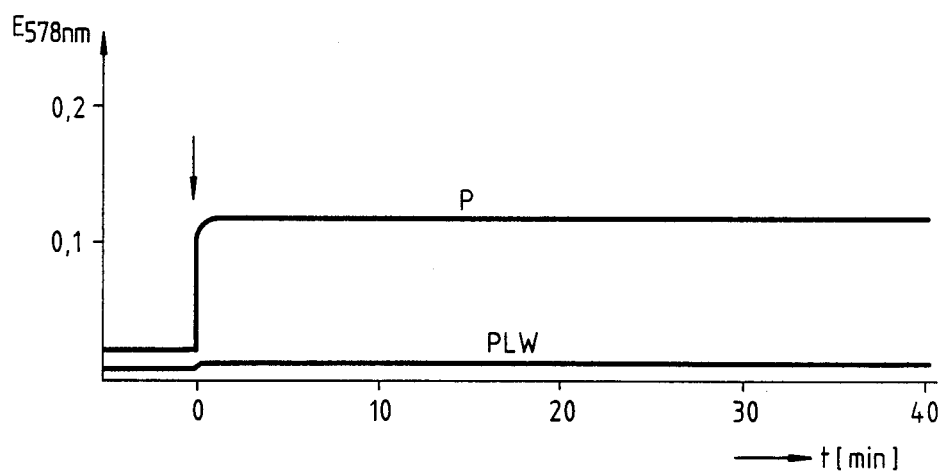
FIG. 1 shows the chronological change of the measurement signal in the case of an iron determination with a reagent according to the present invention, P being sample and PLW being sample blank value.

The chronological course of the sample and blank value signal is to be seen from FIG. 1.

The iron content in the sample is calculated according to the following equations:
$Fe\ (ug./dl.) = E \times 1330$ for the measurement at 578 nm
$Fe\ (ug./dl.) = E \times 1220$ for the measurement at 562 nm.

Example 2

Figure 2:
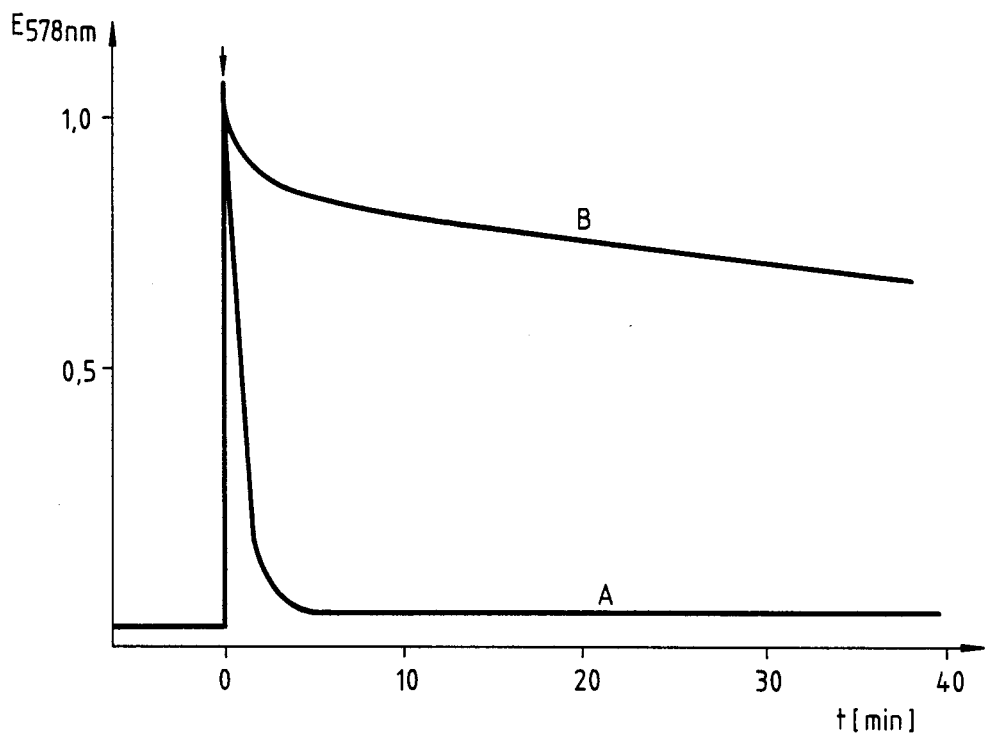
FIG. 2 shows the clarification of lipemic sera, "A" being a reagent according to the present invention and "B" only guanidine hydrochloride.

A strongly lipemic serum which contained 1900 mg/dl. of triglycerides was used. For this purpose, 200 ul. of the serum were mixed with 1 ml. of blank value reagent according to Example 1 and the course of the extinction measured at 25° C. and 578 nm. The result is to be seen from curve A in FIG. 2. Furthermore, for comparison, 200 ul of the serum were mixed with a reagent which consisted of 4.5M guanidine hydrochloride, 0.15M acetate buffer (pH 5.0) and 0.023M ascorbic acid. Here, too, the course of the extinction was measured at 25° C. and 578 nm. The result is to be seen from curve B in FIG. 2. As a comparison of the two curves A and B shows, with a reagent which only contains acetate buffer and guanidine hydrochloride, only a very limited and, in addition, chronologically unstable clarification is obtained. With the reagent according to the present invention, on the one hand, the lipemic serum can be completely clarified within about 7 minutes, the clarification remaining over a period of time of more than 30 minutes.

Example 3

Figure 3:
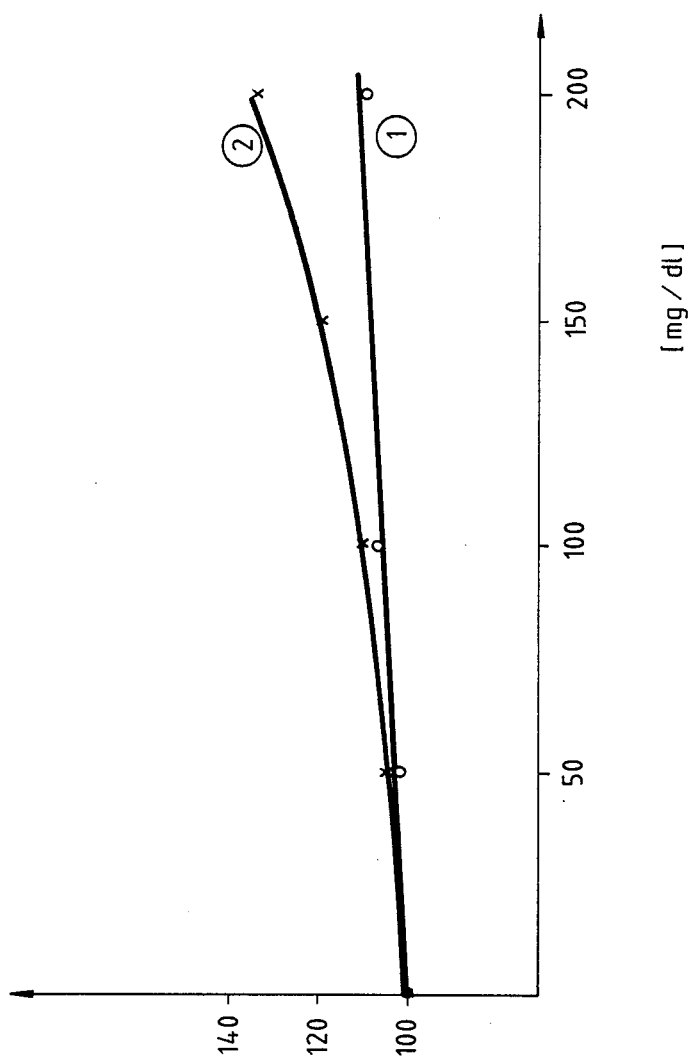
FIG. 3 shows the influence of hemolytic sera on the finding again, 1 being the reagent according to the present invention and 2 a reagent according to U.S. Pat. No. 4,579,825.

A non-hemolytic serum was made up stepwise with hemoglobin to concentrations of up to 200 mg./dl. and the iron content determined as described in Example 1, on the one hand, with the reagent according to the present invention and, on the other hand, with a reagent as is described in U.S. Pat. No. 4,579,825. The result is to be seen from FIG. 3. It is thereby shown that with the reagent according to the present invention, even at very high hemoglobin values, only insignificantly enhanced recovery values are obtained, whereas in the case of the known reagent, even slightly increased hemoglobin values disturb.

Example 4

The iron content was determined in 3 different sera which originated from gammopathic patients. In the case of the determination with the reagent according to the present invention, a measurement signal is achieved which, for a period of 60 minutes, no longer changes which means that no turbidity occurs during this period of time. In contra-distinction thereto, in the case of the use of the known reagent, after commencement of the color formation reaction, a rapid turbidification is shown which leads to a disturbance in the case of photometric measurement.

Example 5

There was examined the solubility of the reagents used, the dissolving off of the iron from its carrier protein, the clarification of lipemic sera, the turbidification by gammopathic sera and the disturbance by hemolytic sera. The results obtained are shown in the following Table.

TABLE

| reagent additives | solubility of the reagent | dissolving off of iron | clarification of lipaemic sera | turbidification by gammopathic sera | disturbance by haemolytic sera |
|---|---|---|---|---|---|
| 1. anionic detergent (sec. alkane-sulphonate, Hostapur) | + | + | +/− | − | − |
| 2 non-ionic detergent (alkanol-polyglycol ether, Oxatal ID104) | − | o | + | o | o |
| 3. non-ionic detergent (fatty acid polyethylene glycol ester, PEG-400-monolaurate | + | − | − | o | o |
| 4. guanidine hydrochloride | + | + | − | + | + |
| 5. combination 1 + 2 | + | + | + | − | − |
| 6. combination 2 + 3 | + | − | + | o | o |
| 7. combination 1 + 4· | − | o | o | o | o |
| 8. combination 2 + 4 | − | + | o | o | o |
| 9. combination 3 + 4 | + | + | − | o | o |
| 10. combination 1 + 2 + 4 | − | o | o | o | o |
| 11. combination 1 + 3 + 4 | − | o | o | o | o |
| 12. combination 2 + 3 + 4 | + | + | + | + | + |

+ means the criterion is fulfilled (e.g. reagent is soluble, no turbidification by gammopathic sera)
− means the criterion is not fulfilled (e.g. unsatisfactory dissolving off of iron, unsatisfactory recovery in the case of haemolytic samples)
o means not measured because the reagent is already unsuitable due to non-fulfillment of other criteria The solubility of the reagent was assessed visually. In the lines characterized with -, there occurred either strong turbidities or precipitations in a concentration range of 1 to 15% by weight.

The assessment of the dissolving off of iron took place by iron determination as described in Example 1. The conditions were regarded as being fulfilled when, in the case of the use of a control serum as sample, the iron content was recovered in an amount of more than 95%.

Sufficient clarification of lipemic sera is ensured when, in the course of an experiment according to Example 2, extinction $E_{578}$ of less than 0.05 is achieved after at most 7 minutes at 25° C. and remains constant for a further 30 minutes.

The turbidity by gammopathic sera was assessed analogously to Example 4 and the recovery in the case of hemolytic sera analogously to Example 3.

It will be understood that the specification and examples are illustrative but not limitative of the present invention and that other embodiments within the spirit and scope of the invention will suggest themselves to those skilled in the art.

We claim:

1. Method for determining iron in a body fluid sample comprising adding to a body fluid sample a fatty acid polyethylene glycol ester, an alkanol polyglycol ether, guanidine hydrochloride in a concentration of at least 1 mole/liter of sample to liberate said iron, reducing said iron to $Fe^{2+}$, adding a color forming reagent which forms a photometrically evaluatable complex with $Fe^{2+}$, and photometrically measuring said complex as a measure of iron in said sample.

2. Method of claim 1, wherein said guanidine hydrochloride is added in an amount of from 3 to about 6 moles/liter of sample.

3. Method of claim 1, wherein said alkanol polyglycol ether is an ether of an 8–12 carbon atom linear or branched chained alkanol and a polyglycol having 3 to 6 glycol units per molecule.

4. Method of claim 1, wherein said alkanol polyglycol ether is an ether of an isodecanol with a polyglycol having 4 glycol units per molecule.

5. Method of claim 1, wherein said reducing agent is ascorbic acid.

6. Method of claim 1, wherein said color system comprises a compound selected from the group consisting of bathophenanthroline and 3-(2-pyridyl)-5,6-bis(4-phenyl-sulfonic acid)-1,2,4-triazine-disodium salt.

7. Method of claim 1, comprising adding a buffer to said sample to adjust pH thereof to a range of from about 5 to about 6.

8. Method of claim 7, wherein said buffer is an acetate buffer and said buffer is added at a concentration of from about 20 to about 500 mmole/liter.

9. Method of claim 1, comprising adding said fatty acid polyethylene glycol ester at a concentration of from about 2.5% to about 15%.

10. Method of claim 9, comprising adding said fatty acid polyethylene glycol ester at a concentration of from about 5% to about 10%.

11. Method of claim 1, comprising adding said alkanol polyglycol ether at a concentration of from about 0.5 to about 5%.

12. Method of claim 11, comprising adding said alkanol polyglycol ether at a concentration of from about 1% to about 3%.

13. Method of claim 1, wherein said fatty acid polyethylene glycol ester is an ester of a linear fatty acid containing from 10 to 14 carbon atoms and a polyethelene glycol of an average molecular weight of from about 200 to about 600.

14. Method of claim 13, wherein said fatty acid polyethylene glycol ester is a monoester.

15. Method of claim 13, wherein said fatty acid polyethylene glycol ester is polyethylene glycol monolaurate.

* * * * *